United States Patent [19]

Strömmer

[11] Patent Number: 5,099,503
[45] Date of Patent: Mar. 24, 1992

[54] METHOD AND DEVICE FOR CONTROLLING THE OPERATION OF A MAMMOGRAPHIC X-RAY APPARATUS

[75] Inventor: Pekka Strömmer, Espoo, Finland
[73] Assignee: Planmed Oy, Finland
[21] Appl. No.: 616,056
[22] Filed: Nov. 20, 1990
[51] Int. Cl.⁵ ............................................... A61B 6/04
[52] U.S. Cl. .................................. 378/37; 378/95; 378/208
[58] Field of Search ................. 378/37, 208, 195, 204, 378/117, 95

[56] References Cited

U.S. PATENT DOCUMENTS 4,658,409 4/1987 Summ ..................................... 378/37
4,744,099 5/1988 Huettenrauch et al. ............. 378/157

Primary Examiner—Janice A. Howell
Assistant Examiner—David P. Porta
Attorney, Agent, or Firm—Jones, Askew & Lunsford

[57] ABSTRACT

Method and device for controlling the operations of a mammographic X-ray apparatus. In the apparatus the breast (4) to be photographed is pressed between a press plate (2) and a film cassette (5) or an equivalent depicting member. In the method the compression force (F) applied by the holder means to the breast (4) to be photographed, or a quantity that represents this force (F) indirectly, is measured. On the basis of the measurement, the velocity (V) of the compression movement of the press mechanism is regulated. The apparatus comprises a C-arm (1), at one of whose ends the X-ray tube (6) is placed and at the other end the film cassette (5). The C-arm (1) is rotatable around a shaft (8) by means of a motor (9). The device comprises a detector (3) or a series of detectors which measures the compression force and by means of which the operation of the press motor (7) for the breast holders is arranged to be controlled.

7 Claims, 2 Drawing Sheets

METHOD AND DEVICE FOR CONTROLLING THE OPERATION OF A MAMMOGRAPHIC X-RAY APPARATUS

The invention concerns a method for controlling the operations of a mammographic X-ray apparatus, in which apparatus the breast to be photographed is pressed between a press plate and a film cassette or an equivalent depicting member.

Further, the invention concerns a device for controlling the operations of a mammographic apparatus, said mammographic apparatus comprising a C-arm or equivalent, at one of whose ends the X-ray tube is placed and at the other end the film cassette, and said C-arm or equivalent being rotatable around a shaft, preferably a horizontal shaft, in relation to the frame of the apparatus by means of a motor, and said C-arm including the film cassette and the press plate as well as a press motor.

In mammographic photographing, in order that the photographing should be successful, it is essential that the object to be photographed is placed in the apparatus so that it is in a correct position and forms a layer of minimum thickness so that the amount of secondary radiation scattered from the breast tissue can be minimized. In order that the pressing could be carried out as well as possible while, nevertheless, keeping the discomfort caused to the patient as little as possible, in prior art mammographic apparatuses have been provided with monitor means for the compressed thickness and compression force of the object to be photographed, the function of said means being to aid the nurse when the breast is being pressed. In some prior-art apparatuses, an excessively high compression force additionally stops the compression movement or releases the press mechanism, thereby preventing an inadvertent excessively intensive compression.

In respect of the prior art related to the present invention, reference is made to the FI Patent Applications (applicant Automed Oy) Nos. 882490 and 894903.

The object of the present invention is to provide a novel method and device for controlling the operations of a mammographic X-ray apparatus so that the operation of the apparatus is more flexible, safer, and more agreeable to the patient to be photographed.

It is a further object of the invention to provide a device that facilitates correct positioning of the breast both for the nurse and for the patient.

The control method and device in accordance with the present invention are particularly well suitable for a mammographic apparatus similar to that described in the above FI Pat. Appl. No. 894903 (date of origin May 26, 1988), wherein a particularly advantageous mode and arrangement of equipment are used for pressing a breast in connection with photographing between the holders. An object of the present invention is to provide certain advantages of synergism with said FI patent application. On the other hand, it should be emphasized that the present invention is also suitable for use in a great variety of other mammographic X-ray apparatuses which are known in prior art or which may be developed later.

In view of achieving the objectives stated above and those that will come out later, the invention is mainly characterized in that in the method the compression force applied by the holder means to the breast (4) to be photographed, or a quantity that represents this force indirectly, is measured and that, on the basis of said measurement, the velocity of the compression movement of the press mechanism is regulated.

On the other hand, the device in accordance with the invention is mainly characterized in that the device comprises a detector or a series of detectors which measures the compression force and by means of which the operation of the press motor for the breast holders is arranged to be controlled.

In the invention, it has been realized, in a novel way, to utilize the breast compression force, which has been measured in a way known in prior art, besides for monitoring and for switching-off the compression, also for control of the apparatus in a considerably more versatile way than in prior art.

In the solution in accordance with the present invention, on the basis of the measurement of compression force, the velocity of the compression movement of the press mechanism, the velocity of the up/down movement of the apparatus, the movement of rotation of the stand, and/or the X-ray generator, or only some of them, are regulated. The invention is primarily intended for use in a mammographic apparatus in which said movements are motorized, so that the mechanical actuators can be integrated in the control system in a novel way.

In the following, the invention will be described in detail with reference to some exemplifying embodiments of the invention illustrated in the figures in the accompanying drawing, the invention being not confined to the details of said embodiments.

Figure 1:
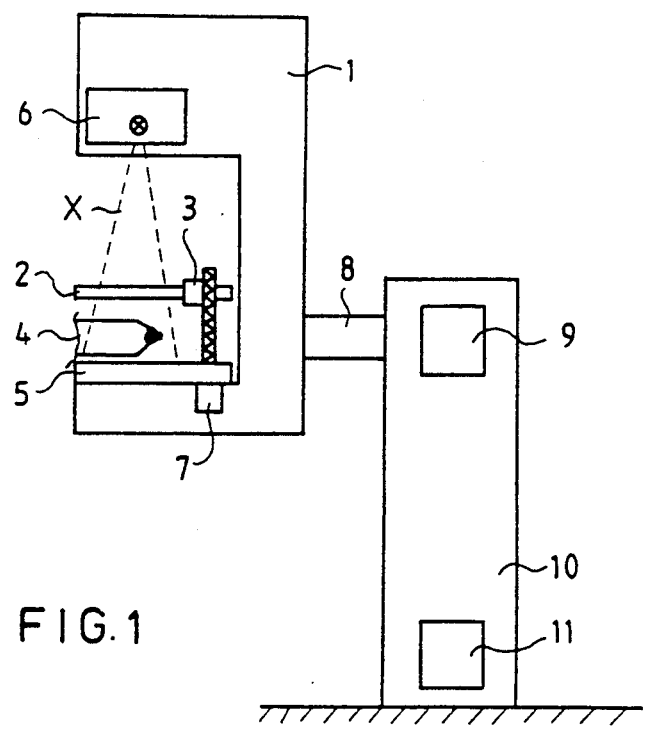
FIG. 1 is a schematic side view of the construction of the apparatus.

To begin with, the basic construction of the mammographic apparatus shown in FIG. 1 will be described. The photographing stand consists of a C-arm 1, at one of whose ends the X-ray tube 6 is fitted, whereas the film cassette 5 is placed at the other end. The C-arm 1 can be rotated around the shaft 8 in relation to the frame 10 of the apparatus by means of a motor 9. For photography, the breast 4 to be photographed is pressed between the film cassette 5 and the press plate 2 by means of the press motor 7, at the same time as the compression force is measured by means of a detector 3. The height of the C-arm 1 is regulated by means of a motor 11.

In respect of further details of construction of the X-ray apparatus shown schematically in FIG. 1, reference is made to the FI Patent Applications Nos. 882490 and 894903 mentioned above.

Figure 2:
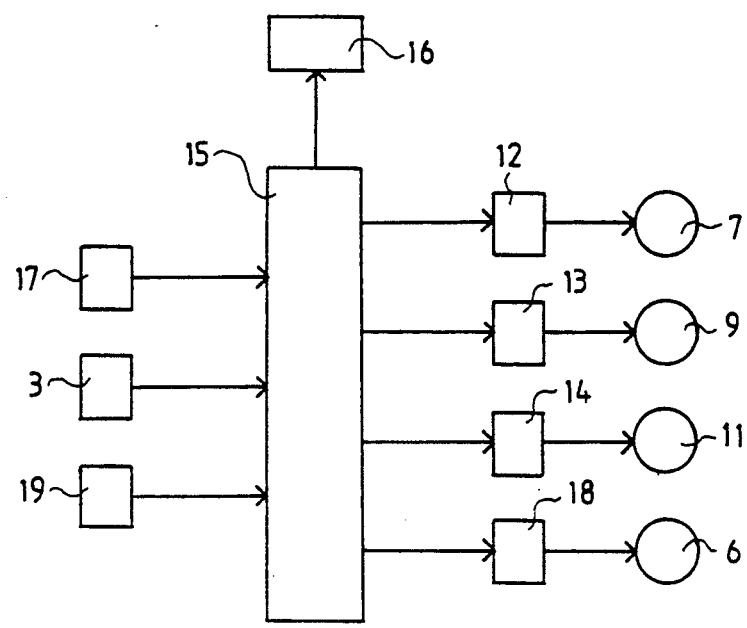
FIG. 2 shows the measurement and control system as a block diagram.

FIG. 2 shows the construction of the control system as a block diagram. The control unit 15 receives the control data from a set member 17, which may be, for example, a keyboard. Also, the control unit 15 monitors the operation of the stand by means of limit detectors 19 and a compression-force measurement detector 3. On the basis of these data, the control unit 15 sets the data of the monitor 16 and controls the press motor 7 by the intermediate of the controller 12, the rotation motor 9 by the intermediate of the controller 13, and the lifting motor 11 by the intermediate of the controller 14. Also, the control unit 15 controls the generator 18 and further, by its means, the X-ray tube 6. The detailed construction of the control unit 15 itself will not be discussed in more detail in this connection, because its embodiment has no relevance to the present invention. For example, the control unit may be a microprocessor with necessary auxiliary equipment.

An object of the invention is to facilitate the photographing operation and to prevent damage in a situation in which the breast 4 is already partly pressed between the film cassette 5 and the press plate. In the solution in accordance with the present invention, compression measurement is used in accordance with the diagram shown in FIG. 2 for controlling the operation of the apparatus in accordance with the following description.

As a rule, the process of photography proper proceeds so that first the desired projection of photography is chosen, which determines the position of rotation of the C-arm 1, of which positions the five most typical ones are vertical position, horizontal positions rotated to either direction, and positions inclined to either direction by about 45 to 60 degrees. Thereupon the holder stand is placed at a level in accordance with the height of the person to be photographed and the breast 4 is placed between the press plate 2 and the film cassette 5 and pressed in its place, whereupon the photographing is carried out by means of an X-ray beam X.

Figure 3:
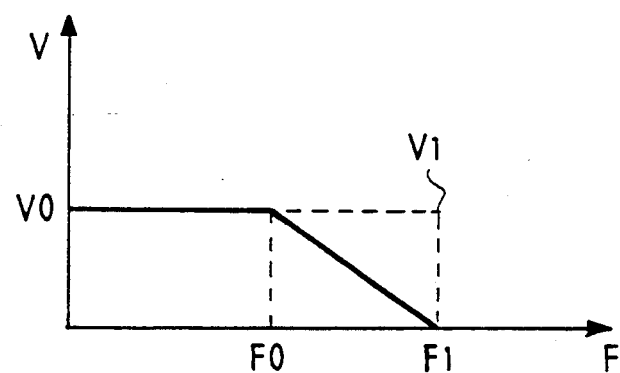
FIG. 3 illustrates the velocity of the press motor as a function of the compression force.

When the breast 4 is compressed by means of the press plate 2, in the invention the velocity of the press motor 7 is made slower as the compression force is increasing until, after the maximum permitted compression force has been reached, the press motor 7 stops completely and prevents excessive compression forces. In FIG. 3 this is shown as a graph, wherein the vertical axis V represents the velocity of the press motor 7 and the horizontal axis F represents the compression force. Initially, the press motor 7 is run at a relatively high invariable velocity V0, but when the measured compression force reaches a predetermined limit F0, the velocity V starts being slowed down until, after the force F has reached a predetermined limit F1, the velocity V has been regulated to zero.

The dependence of the press velocity V on the measured force F may be linear or non-linear. A high initial velocity V0 permits pre-compression of the breast 4 quickly, which is desirable because this stage is difficult and requires holding of the breast 4 in its place by hand until the press plate 2 starts positioning the breast 4 stably. After a reasonable compression has been reached, the velocity V starts slowing down, whereby a careful and accurate compression is accomplished and there is no risk of unnecessarily high compression force as a result of an excessively high velocity.

During slow pressing, the correct compression strength of the breast 4 can be measured accurately, whereby it is possible to employ just a compression force as high as is really necessary to take a good photograph. It is a well-known fact that the operation is usually disagreeable for the patient, and therefore the compression strength should be kept at such a level that at least it does not cause actual pain to the patient to be photographed.

In FIG. 3, the dashed line V1 illustrates the compression velocity of the prior-art solutions, which remains invariable until the present limit $F_1$ of compression force is reached and the press movement is suddenly stopped. In this method, the breast is usually compressed up to the limit, whereupon the pressing is continued manually by means of a mechanism separately provided in the apparatus for this purpose. Such a solution is operable but mechanically difficult to carry into effect and time-consuming. Moreover, the limit should be set individually for each patient based on sensing of the properties of the breast, but, as a rule, the limit remains fixed at a value sufficiently high for all cases.

Figure 4:
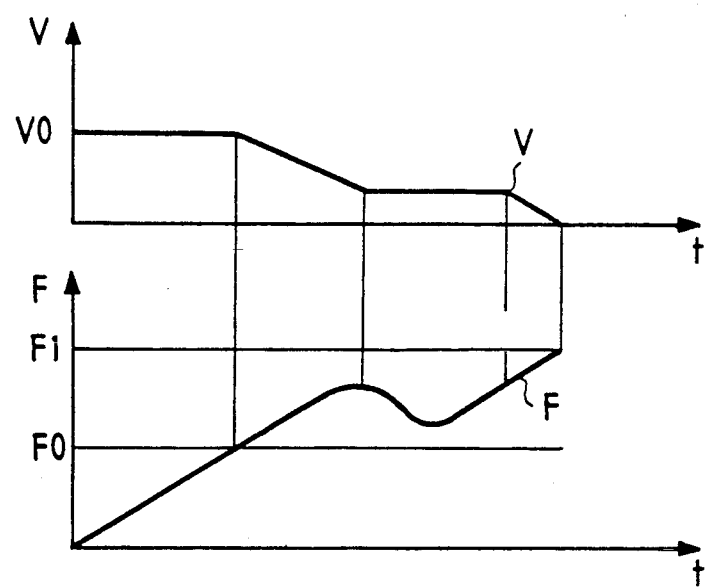
FIG. 4 illustrates the press velocity as a function of the compression force in a preferred special case.

FIG. 4 illustrates a special application of the invention. To start with, the compression velocity is invariable V0 and, when the force F reaches a predetermined level F0, the compression velocity V starts being slowed down in the way described above. However, if the compression force F is lowered during further compressing, the velocity V is not increased accordingly, but the velocity is kept at the value to which it has been slowed down. When the force F becomes higher further, the velocity is slowed down in the way described above until, when the force F reaches a predetermined limit F1, the velocity has been lowered to zero. A situation of this sort may arise, for example, when a press plate described in the FI Pat. Appl. No. 894903 is used, in which case an increase in the velocity in between may seem scaring, and in this way a disagreeable situation is eliminated.

Occasionally, the compression must also be reduced during positioning of the breast 4. In such a case, the releasing can be carried out either rapidly at full velocity or slowly by increasing the velocity in relation to the compression force. It is known in prior art to open the compression quickly, but in such a case the compression may be opened excessively and the breast no longer remains in the desired position, in which case the positioning must be restarted from the beginning. In the solution in accordance with the invention, the opening of the compression can be accomplished optionally either quickly or in relation to the compression force, whereby said drawbacks are avoided.

When the breast 4 is partly compressed, occasionally there is still a need to adjust the height of the C-arm 1. In the solution in accordance with the present invention, a raising movement is in such a case permitted by the control system, but only at a very slow velocity if the compression measurement ascertains that there is a compression. As a rule, in prior-art mammographic apparatuses, the raising movement is carried out manually, in which case a height adjustment with the patient partly compressed is impossible or very difficult, and if it is carried out by means of a motor, careless operation of the apparatus may result in a height adjustment at an excessively high velocity, which is quite a scaring experience for the patient fixed to the C-arm 1. In the solution in accordance with the invention, adjustment of the height of the C-arm 1 is easy and, at the same time, more agreeable to the patient.

The movement of rotation of the C-arm 1 around the shaft 8 is, as a rule, carried out manually, but motor-operated solutions also exist. In the solution in accordance with the invention, the control of the compression measurement is also employed for controlling the movement of rotation so that it prevents movement of rotation as long as compression can be noticed. In motorized models, the prevention can be accomplished by preventing control of the motor, and in manual models by locking the movement, for example, by means of a solenoid. As an exceptional case, in motorized models, it is possible to permit a rather short slow rotation, for example, necessary in stereo photography, wherein the breast holders are not permanently fixed to the movement of rotation of the C-arm but, nevertheless, the patient supports herself on the C-arm 1. A high-speed rotation is not desirable when the patient is under compression.

A novel feature, which may be combined with the invention when necessary, is the use of compression measurement also in the control of the X-ray generator 6. X-ray radiation can be prevented if the compression measurement does not find a sufficiently high compression force. In such a case, inadvertent irradiation or photography of a deficiently positioned breast is prevented, which is a substantial advantage.

It should be emphasized that above only some exemplifying embodiments of the invention have been described and that the scope of the invention also includes many modifications of the method and the device in accordance with the invention which are obvious for a person skilled in the art.

In the following, the patent claims will be given, and the various details of the invention may show variation within the scope of the inventive idea defined in said claims.

I claim:

1. Method for controlling the operations of a mammographic X-ray apparatus, wherein a breast (4) to be photographed is pressed between a press plate (2) and a film cassette (5) or an equivalent depicting member by a press mechanism, comprising the steps of:
    measuring a compression force (F) applied by a holder means to the breast (4) to be photographed, or a quantity that indirectly represents the force (F); and
    on the basis of said measurement, regulating the velocity (V) of compression movement of the press mechanism by lowering the velocity (V) starting from a certain force (F0) in a substantially linear way until a maximal compression force (F1) is reached, whereupon the compression movement is stopped.

2. Method as in claim 1, wherein the breast holder means is controlled to a compression position initially at a substantially invariable velocity (V0) until the compression force reaches a certain preset value (F0), whereupon the compression velocity (V), controlled by the force measurement, is lowered until a maximal compression force (F1) is reached, by which time the velocity has been adjusted to zero.

3. Method as in claim 1, characterized in that the compression on the breast (4) is released during positioning of the breast, and that the releasing of the compression is carried out either at full velocity or at partial velocity while correspondingly increasing the velocity as the compression force becomes lower.

4. Method as in claim 1, wherein a control responsive to measurement of compression force (F) is used in the control of movement of a C-arm (1) or equivalent of the mammographic apparatus so that a movement of rotation of the C-arm is substantially prevented when a compression force is detected.

5. Method as in claim 1, wherein by means of measurement of the compression force of the breast holder means, an X-ray generator (6) associated with the apparatus is controlled so that X-ray radiation is prevented at compression forces lower than a certain value.

6. Method for controlling the operations of a mammographic X-ray apparatus, wherein a breast (4) to be photographed is pressed between a press plate (2) and a film cassette (5) or an equivalent depicting member by a press mechanism, comprising the steps of:
    measuring a compression force (F) applied by a holder means to the breast (4) to be photographed, or a quantity that indirectly represents the force (F); and
    on the basis of said measurement, regulating the velocity (V) of compression movement of a press mechanism so that, after a certain compression movement of invariable velocity (V0), the compression velocity is lowered until the compression force reaches a certain preset value (F0), whereupon the compression is continued with a lower substantially invariable velocity; and
    carrying out the final stage of compression while slowing the velocity (V) towards zero until a preset maximal compression force (F1) is reached.

7. Apparatus for controlling the operation of a mammographic X-ray apparatus including a press plate and a film cassette or equivalent depicting member, and means for applying compression to the breast, comprising:
    means for measuring a quantity representing the compression force applied to the breast; and
    means responsive to said quantity to lower velocity of the compression-applying means starting from a certain force (F0) in a substantially linear way until a maximal compression force (F1) is reached, whereupon the compression movement is stopped.

* * * * *